(12) United States Patent
Olivares-Amaya et al.

(10) Patent No.: US 11,789,906 B2
(45) Date of Patent: Oct. 17, 2023

(54) SYSTEMS AND METHODS FOR GENOMIC MANIPULATIONS AND ANALYSIS

(71) Applicant: ARC BIO, LLC, Cambridge, MA (US)

(72) Inventors: Roberto Olivares-Amaya, Somerville, MA (US); David Andrew Sinclair, Chestnut Hill, MA (US); Alejandro Quiroz-Zarate, Cambridge, MA (US); Thomas J. Watson, Jr., Newton, MA (US)

(73) Assignee: ARC BIO, LLC, Cambridge, MA (US)

( * ) Notice: Subject to any disclaimer, the term of this patent is extended or adjusted under 35 U.S.C. 154(b) by 1263 days.

(21) Appl. No.: 15/524,319

(22) PCT Filed: Nov. 19, 2015

(86) PCT No.: PCT/US2015/061548
§ 371 (c)(1),
(2) Date: May 4, 2017

(87) PCT Pub. No.: WO2016/081712
PCT Pub. Date: May 26, 2016

(65) Prior Publication Data
US 2017/0357665 A1 Dec. 14, 2017

Related U.S. Application Data

(60) Provisional application No. 62/081,931, filed on Nov. 19, 2014.

(51) Int. Cl.
*G06F 16/174* (2019.01)
*G16B 50/00* (2019.01)
*G16B 50/50* (2019.01)

(52) U.S. Cl.
CPC ......... *G06F 16/1744* (2019.01); *G16B 50/00* (2019.02); *G16B 50/50* (2019.02)

(58) Field of Classification Search
CPC .............................................. C12Q 2600/158
See application file for complete search history.

(56) References Cited

U.S. PATENT DOCUMENTS

| | | | |
|---|---|---|---|
| 5,750,341 A | 5/1998 | Macevicz | |
| 6,306,597 B1 | 10/2001 | Macevicz | |
| 7,115,400 B1 | 10/2006 | Adessi | |
| 7,211,390 B2 | 5/2007 | Rothberg | |
| 7,232,656 B2 | 6/2007 | Balasubramanian | |
| 7,244,559 B2 | 7/2007 | Rothberg | |
| 7,264,929 B2 | 9/2007 | Rothberg | |
| 7,323,305 B2 | 1/2008 | Leamon | |
| 7,948,015 B2 | 5/2011 | Rothberg | |
| 2008/0160580 A1 | 7/2008 | Adessi | |
| 2008/0286795 A1 | 11/2008 | Kawashima | |
| 2009/0026082 A1 | 1/2009 | Rothberg | |
| 2010/0328805 A1 | 12/2010 | Brittner et al. | |
| 2011/0262920 A1 | 10/2011 | Yen et al. | |
| 2011/0288785 A1 | 11/2011 | Tembe | |
| 2012/0330567 A1 | 12/2012 | Bauer et al. | |
| 2013/0246460 A1* | 9/2013 | Maltbie | G16B 20/00 707/771 |
| 2013/0267443 A1* | 10/2013 | Chinnaiyan | C12Q 1/6886 506/39 |
| 2013/0282677 A1 | 10/2013 | Ji et al. | |
| 2013/0338017 A1* | 12/2013 | DuBridge | C12N 15/1037 506/9 |
| 2015/0066385 A1* | 3/2015 | Schnall-Levin | G16B 30/00 702/20 |
| 2015/0227685 A1 | 8/2015 | Kural | |
| 2016/0160295 A1* | 6/2016 | Chinnaiyan | C12Q 1/6886 506/2 |
| 2016/0239604 A1* | 8/2016 | Chudova | G16B 25/00 |
| 2016/0298183 A1* | 10/2016 | Wen | C12Q 1/6827 |

FOREIGN PATENT DOCUMENTS

WO 2009046445 4/2009

OTHER PUBLICATIONS

Shendure et al. Next-generation DNA sequencing Nature Biotechnology vol. 26, pp. 1135-1145 (Year: 2008).*
International Search Report and Written Opinion from PCT/US2015/61548, dated Feb. 12, 2016, 7 pages.
Devereux, J. et al. "A comprehensive set of sequence analysis programs for the VAX." Nucleic acids research 12.1Part1 (1984): 387-395.
Gudmundsson, J., et al. "Genome-wide association and replication studies identify four variants associated with prostate cancer susceptibility." Nature genetics 41.10 (2009): 1122.

(Continued)

*Primary Examiner* — John S Brusca
(74) *Attorney, Agent, or Firm* — QUARLES & BRADY LLP

(57) ABSTRACT

Method and systems for preparing and analyzing a DNA sample from a subject are provided herein. Also provided are methods and systems for obtaining, analyzing, and manipulating genomic and proteomic sequence data. In particular, methods and systems provided herein involve transformation of raw genetic or proteomic sequence into a compressed data set and transmission of the compressed data set using a fixed binary encoding scheme capable of compressing the data by up to 75%. An interface is in communication with the compression module and configured to display transmitted genomic and proteomic sequence data.

25 Claims, 4 Drawing Sheets

(56) References Cited

OTHER PUBLICATIONS

MacLean, D. et al. "Application of 'next-generation' sequencing technologies to microbial genetics." Nature Reviews Microbiology 7.4 (2009): 287.
Margulies, M., et al. "Genome sequencing in microfabricated high-density picolitre reactors." Nature 437.7057 (2005): 376.
Out, A.A., et al. "Deep sequencing to reveal new variants in pooled DNA samples." Human mutation 30.12 (2009): 1703-1712.
Soni, G. V., et al. "Progress toward ultrafast DNA sequencing using solid-state nanopores." Clinical chemistry 53.11 (2007): 1996-2001.
Turner, E. H., et al. "Massively parallel exon capture and library-free resequencing across 16 genomes." Nature methods 6.5 (2009): 315.
Voelkerding, K. V. et al. "Next-generation sequencing: from basic research to diagnostics." Clinical chemistry 55.4 (2009): 641-658.

\* cited by examiner

FIG. 1

| Amino Acid | 3-Letter Abbreviation | Single-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Glu | Q |
| Glutamic Acid | Gln | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tryosine | Tyr | Y |
| Valine | Val | V |

SYSTEMS AND METHODS FOR GENOMIC MANIPULATIONS AND ANALYSIS

CROSS-REFERENCE TO RELATED APPLICATIONS

This application is a 371 U.S. National Phase Entry of PCT/US2015/061548, filed Nov. 19, 2015, which claims the benefit of U.S. Provisional Application Ser. No. 62/081,931, filed Nov. 19, 2014, each of which is incorporated herein by reference in its entirety.

STATEMENT REGARDING FEDERALLY SPONSORED RESEARCH

Not applicable.

BACKGROUND OF THE INVENTION

The field of the invention is biological sequence manipulation and analysis. More particularly, the invention relates to systems and methods for manipulating and analyzing genomic sequencing data.

Biological sequencing is the process of determining the order of individual units, e.g., nucleotides, within biomolecules, such as DNA, RNA, and polymers. The rapid development of sequencing methods and instruments has significantly advanced biomedical studies. Next-generation sequencing (NGS) technologies, which parallelize the sequencing process, have created a new paradigm for low-cost, high-throughput sequencing process. Novel sample preparation techniques continue to improve the ability of NGS to produce improved sequence data which can result in improved genome assemblies. Long range sequencing technologies, which produce longer sequence reads are improving and are poised to provide even more high quality sequence data. The speed, read length, and precision of sequencing technology continues to improve, and cost of sequencing continues to drop.

Sequencing technologies enable researchers, doctors, governments, and increasingly non-medical and non-technical people, to collect large amounts of high-precision sequence data within a shorter time. Whole genome DNA and RNA sequencing is increasingly becoming routine in research, medicine, law enforcement, and medicine. For example, whole genome DNA and RNA sequencing is used for genetic testing, forensics, archeology, paleontology, and for disease diagnosis and treatment. Other non-nucleic acid based sequencing technologies also continue to advance. For example, advances in mass spectrometry have greatly increased the ability to generate vast amounts of ordered proteomic and small molecule data.

Typically, sequence data is archived in repositories. Individual repositories associated with laboratories generating the sequence data exist as often non-connected non-standardized collections to store the lab specific data locally or using a cloud based solution. Sequencing providers are increasingly building commercial repositories for customer use which are often limited to users of a particular sequencing technology. Medical groups are struggling starting to build repositories of their patent populations sequence data, which are designed to both be compliant with patent privacy concerns and work with already existing medical record systems. Public sequence repositories, which archive data received from various sources in a central repository continue to proliferate, but the methodology to build and store data in these large scale databases continues to be debated. Storage of such large volumes of data requires repositories to have large storage capability with vast volumes of storage capacity. Advances in technology are rapidly increasing the amount of genomic data, further increasing maintenance costs and storage space requirements. Furthermore, since the genomic data may be utilized for future references, the genomic data may need to be archived in compressed form so as to decompress/retrieve the same without any loss of information.

The ability to sequence biomolecules cheaply and quickly, generating vast amounts of data, has led to severe bottlenecks and limitations on how that data can be used. For example, data transmission, processing (e.g., alignment and assembly) and storage is increasingly exceeding current technologies. Computers, for example, have limitations on handling and compressing such data, and the systems to transmit such amounts of data in a rapid and secure way are also limiting the usefulness of sequencing and mass spectrometry data. Thus, there is a need for systems and methods for quickly and efficiently compressing, transmitting, storing, and presenting compressed and decompressed genomic and proteomic data for visual display.

SUMMARY

The present disclosure overcomes the aforementioned drawbacks by providing methods and systems for genomic manipulation and analysis. For example, provided herein are methods and systems for compressing genome sequencing data and proteomic data by up to 75% by assigning a 2-bit representation to base pairs. Thus, as sequencing data is transmitted or processed in bytes, four base pairs per byte may utilized.

In a first aspect, provided herein is a method for preparing and analyzing DNA. The method comprises obtaining from a subject a sample, where the sample comprises DNA; preparing the sample for DNA sequencing to obtain a prepared sample; performing a sequencing reaction on the prepared sample using a sequencer to obtain raw sequence information; transmitting the raw sequence information to a compression module; transforming the transmitted raw sequence information into a compressed data set using a fixed encoding scheme on the compression module; transferring the compressed data set to a computer memory, wherein the compressed data set utilizes less than 80% of the memory required for the raw sequence information before compression; and accessing the transferred compressed data set from the computer memory using with a graphical user interface (GUI) the computer memory to retrieve and visualize genomic information. The compressed data set can be associated with the fixed encoding scheme such that the compressed data set is identifiable by the fixed encoding scheme. The method can further comprise identifying in the genomic information at least one nucleotide sequence comprising a plurality of primary characters, each character corresponding to a molecular unit. The molecular unit can be a nucleotide base. The nucleotide base can comprise at least one of adenine (A), thymine (T), guanine (G), and cytosine (C).

In some cases, the method further comprises the step of assigning a binary number to the plurality of primary characters when applying the fixed encoding scheme to the at least one nucleotide sequence. The at least one nucleotide sequence being encoded can be free of quality data. The method can further comprises the step of applying a separate, fixed encoding scheme to the quality data. The raw sequence information can be a FASTQ file. The DNA can be chromosomal, viral, or mitochondrial DNA.

In another aspect, provided herein is a method comprising receiving at least one genomic data set into a compression module configured to encode genomic data at a density of four base pairs per byte; generating, using a fixed encoding scheme on the compression module, a compressed data set, wherein the fixed encoding scheme compresses genomic sequence information of the at least one data set at a density of four base pairs per byte; transferring the compressed data set to a computer memory, wherein the compressed data set utilizes less than 80% of the memory required for the received genomic data set before compression; accessing the transferred compressed data set from the computer memory using a graphical user interface (GUI) the computer memory to retrieve and visualize genomic information. In some cases, non-genomic sequence information of the at least one genomic data set is not encoded at a density of four base pairs per byte and is stored separately from the transferred compressed data set. The method can further comprise the step of applying a separate, fixed encoding scheme to the non-genomic sequence data. Encoding can comprise assigning at least one of adenine (A), thymine (T), guanine (G), and cytosine (C) to a two-bit binary number. The encoding can achieve compression. The compression can be lossless. The compression can be up to 75 percent compared to the received genetic data set prior to encoding. The interface is configured to display genomic data.

In a further aspect, provided herein is a method comprising receiving genomic data via a compression module, wherein the compression module is configured to encode genomic data at a density of four base pairs per byte; and encoding nucleic acid sequence information of the genomic data at a density of four base pairs per byte, wherein the encoding achieves compression such that the compressed, encoded nucleic acid sequence information uses less than 80% of the computer memory required to store the genomic data prior to encoding. In some cases, non-nucleic acid sequence information of the genomic data is not compressed and is stored separately from the encoded nucleic acid sequence information. The method can further comprise reconstructing an uncompressed genomic data set from the compressed nucleic acid sequence information, wherein reconstructing comprises applying a fixed decoding scheme is applied to the encoded nucleic acid sequence information to obtain uncompressed nucleic acid sequence information; retrieving non-nucleic acid sequence information from the separate storage; and adding the non-nucleic acid sequence information to the uncompressed nucleic acid information to obtain a reconstructed genomic data set.

In another aspect, provided herein is a method comprising receiving at least one genomic data set into a compression module configured to encode genomic data; generating, using an encoding scheme on the compression module, a compressed data set; and transferring the compressed data set to a computer memory, wherein, of the bit storing genomic data, the computer memory has an average error rate between one error per $10^{13}$ bases to one error per $10^{16}$ bases of processed, compressed genomic data. The error can be a read error or write error. The computer memory can be a hard disk drive and, of the bits storing genomic data, the hard disk drive can have an average error rate between one error per $10^{15}$ bases and one error per $10^{16}$ bases. The computer memory can be a solid state drive and, of the bits storing genomic data, the solid state drive can have an average error rate between one error per $10^{13}$ bases and one error per $10^{14}$ bases.

The foregoing and other aspects and advantages of the invention will appear from the following description. In the description, reference is made to the accompanying drawings, which form a part hereof, and in which is shown by way of illustration a preferred embodiment of the invention. Such embodiment does not necessarily represent the full scope of the invention, however. Therefore reference is made therefore to the claims and herein for interpreting the scope of the invention.

BRIEF DESCRIPTION OF THE DRAWINGS

FIG. 1 is a conversion table that enables amino acids to be encoded as single alphabetic characters according to a standard supplied by the International Union of Pure and Applied Chemistry (IUPAC).

DETAILED DESCRIPTION

Definitions

Figure 2:
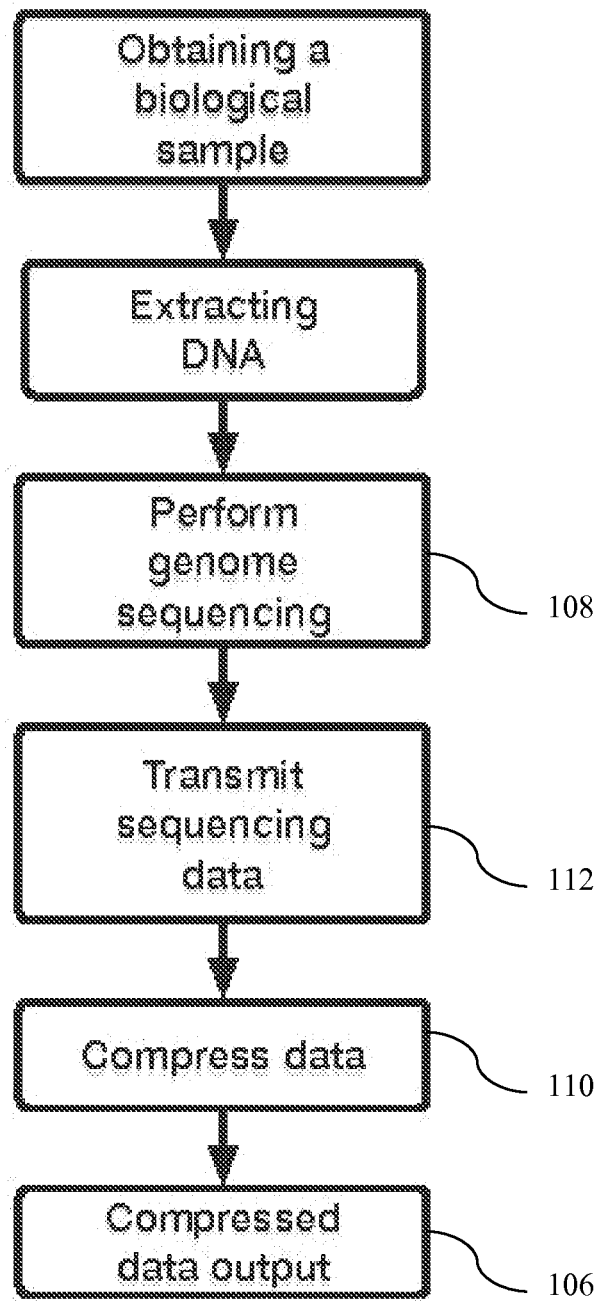
FIG. 2 illustrates a system 100 for compressing genomic and proteomic data. A sequencing reaction is performed in a sequencer 108 using a sample obtained from a patient. The resulting sequence data 112 is transmitted to a compression module 110 for encoding and storage 106.

The below terms are discussed below to illustrate meanings of the terms as used in this specification, in addition to the understanding of these terms by of those of skill in the art. As used in the specification and claims, the singular forms "a", "an" and "the" can include plural references unless the context clearly dictates otherwise. For example, the term "a cell" can include a plurality of cells, including mixtures thereof.

As used herein, the term "alignment" can be any computational process in which sequence strings produced by a sequencer are ordered relative to another sequence, for example by matching a sequence produced by a sequencer to a reference sequence. An alignment can be, for example, a Smith Waterman local alignment, a gapped alignment or semi-gapped alignment. In some instances an alignment matches multiple sequence strings.

Variability in the genome can be represented as "alternative paths." For example a primary genome can be a linear sequence of DNA bases (represented by the letters A, C, T, and G). A secondary genome may have a different sequence of DNA bases which represents the biological diversity between the primary and secondary subject.

"Biological data" include information relating to, for example and without limitation, the genome, proteome, transcriptome, epigenome, metabolome, and other biological systems In other cases, the biological data comprises metabolome data, epigenome data, and/or transcriptome data. As used herein, the term "metabolome" refers to entirety of cellular metabolites, e.g., small chemical or biological molecules (usually of low molecular weight) produced in metabolic reactions. Data of the metabolome (metabolomic data) includes, without limitation, qualitative and quantitative information about metabolite levels and enzyme activities of individual metabolic pathways or interacting metabolic pathways within a biological organism, an organ, a tissue, a cell, or cellular compartment. Metabolomic data are typically archived in various repositories for future analysis. As used herein, the term "epigenome" refers to changes to genetic material that are not reflected at the sequence level such as DNA methylation and chromatin restructuring or remodeling. The "transcriptome" refers to the entirety of gene transcripts (mRNA) synthesized by an organism under certain environmental conditions. A transcriptome data set includes, without limitation, qualitative and quantitative information as to the activation or deactivation of expression of a gene of interest.

"Correlated loci" can mean sequences from two genomes, or a subject genome and a reference genome, which generally represent the same genomic region. It can also mean sequences from one genome but two or more different regions. Correlated loci can be within the same species. Correlated loci can be within the same subject. Correlated loci can be correlated via linkage disequilibrium, conserved regions on a haploid, a priori data such as 1000 genomes or the like.

Genomic information can be "phased." Phased sequences capture chromosomal content, including mutations that may differ across chromosome copies. Phased sequencing can, in some instances, distinguish between maternally and paternally inherited alleles. Phased sequences can be partially phased sequences, where some, but not all, of the chromosomal content is represented.

Typically, genomic data includes a plurality of genomic information and/or a plurality of genetic features. As used herein, the term "genetic feature" refers to any genome, genotype, haplotype, chromatin, chromosome, chromosome locus, chromosomal material, deoxyribonucleic acid (DNA), allele, gene, gene cluster, gene locus, genetic polymorphism, genetic mutation, genetic mutation rate, nucleotide, nucleotide base pair, single nucleotide polymorphism (SNP), restriction fragment length polymorphism (RFLP), variable tandem repeat (VTR), copy number variant (CNV), microsatellite sequence, genetic marker, sequence marker, sequence tagged site (STS), plasmid, transcription unit, transcription product, gene expression level, genetic expression (i.e., transcription) state, ribonucleic acid (RNA), and complementary DNA (cDNA), including the nucleotide sequence and encoded amino acid sequence associated with any of the above. An epigenetic feature is any feature of genetic material—all genomic, vector and plasmid DNA and chromatin—that affects gene expression in a manner that is heritable during somatic cell divisions and sometimes heritable in germline transmission, but that is nonmutational to the DNA sequence and is therefore fundamentally reversible, including but not limited to methylation of DNA nucleotides and acetylation of chromatin-associated histone proteins. As used herein, therefore, genetic sequence data can include, without limitation, nucleotide sequences, deoxyribonucleic acid (DNA) sequences, and ribonucleic acid (RNA).

The term "k-mer" can refer to all the possible subsequences of length k that are contained in a sequence.

A "genome variation map", can be constructed where individual subject genomes which go into the construction of the map will be merged into the reference genome at the points where it matches the primary sequence, with variations appearing as additional alternate paths along the genome. The resulting map will include multiple forms of genomic variation. A genome variation map can be represented as a graph that is not a directed acyclic graph. It can be represented as a de Bruijn graph for example. A genomic variation map can be static, where additional inputs are not used to alter the map. A genomic variation may be dynamic, where the alternative paths are updated or expanded as additional subject genomes are analyzed. In some instances a genomic variation map may be masked to identify alternative paths that match a masking condition.

The term "assembly" can be any computational process in which sequence strings produced by a sequencer or mass spectrometer are merged between one another with the objective to reconstruct the original sequence string, from which the set of all sequence strings were derived. In some instances an assembly is from an individual organism. In some instances multiple individuals are can be used to create an assembly. In some instances an assembly is created de novo, without the use of a reference sequence. In some instances an assembly is created using a reference sequence. The reference sequence can be a genome from the same species. The reference genome can be a genome from a closely related species.

The term "remote alignment" can be any computational process by which alignment of a plurality of sequence data (reads or sequences) is divided into a certain predefined number of independent smaller alignment tasks ("subtasks") with a subset of the plurality of sequence reads. Such independent subtasks can be performed by independent computer devices capable of receiving the subset of sequence reads, aligning the subset of sequence reads, and transmitting the subset of sequence reads to an appropriate computational device. A whole and complete alignment of the original plurality of sequence data can be the accumulation of all the independent subtask alignments.

The term "index" can by any database that is used to optimize the access of data. The database can consist of keys. These keys can be attributes on which the search on the original database is going to be based.

The term "hash table" can describe a method or structure that can allow for accelerated searching within the index.

The term "reference sequence" can refer to a sequence string composed of the information required to define the molecule at hand. For example, a whole human genome would be a sequence of nucleotides consisting of about 3 billion bases to be compliant for the definition of a human genome. A reference genome (alternatively referred to as a "reference assembly") can be a reference sequence. A reference genome can be a digital nucleic acid sequence database, assembled by as a representative example of a set of related nucleic acids. A reference genome can be, for example, an example of a particular specie's genome. In some instances a reference genome can comprise alternative paths. In some cases, the reference genome is a complete genome, representing every nucleotide in the genome. A reference genome can be complete genome, representing every nucleotide in the genome. A reference genome need not be complete. A reference genome may represent up to 50%, 60%, 70%, 80%, 90%, 95%, 99%, or 99.9% of the nucleotides in a genome. A reference genome can come from an individual. A reference genome can be a compilation of information from many individuals.

The term "metadata" can mean data associated with one another. In some instances metadata is different kinds of data linked in a single file. Metadata can vary between different file formats. Metadata can describe the composition of different types structures added in an ordered manner that can be consistent.

"Raw genetic sequence data" are data obtained from sequencing reactions. Raw genetic sequence data can be text-based. Raw genetic sequence data can have a FASTA format. A FASTA format is a text-based format for representing either nucleotide sequences or peptide sequences, in which nucleotides or amino acids are represented using single-letter codes. Raw genetic sequence data can be text-based format for storing both a biological sequence and its corresponding quality scores, for example it can have a FASTQ format. FASTQ format is a text-based format for storing both a biological sequence and its corresponding quality scores. In some instances the sequence letter and quality score are each encoded with a single ASCII character for brevity. In some instances raw genetic sequence data can be converted from one format to another using a format converter. In some instances raw genetic sequence data is called a "read" or a plurality of "reads".

A "sequencing device" is a device that performs a sequencing reaction. Sequencing devices can be used to generate raw genetic sequence data. In some instances the methods described herein can be performed while the sequencing device is performing the sequencing reaction. For example as sequence data is generated by the sequencing device those data can be encrypted and aligned while encrypted. In some instances a sequencing device can output SAM data.

The SAM Format (or "SAM data") is a text format for storing sequence data in a series of tab delimited ASCII columns. SAM data can be generated as a human readable version of its sister BAM Format ("BAM data"), which stores the same data in a compressed, indexed, binary form. SAM format data can be output from aligners that read FASTQ files and assign the sequences to a position with respect to a known reference genome. SAM can also be used to archive unaligned sequence data generated directly from sequencing machines. In some instances SAM data comprises CIGAR sequences. The CIGAR sequence is a sequence of base lengths and the associated operation. They are used to indicate properties, for example which bases align (e.g., either a match/mismatch) with the reference, are deleted from the reference, or are insertions that are not in the reference.

The Variant Call Format (VCF) specifies the format of a text file used for storing gene sequence variations in the interdisciplinary field of bioinformatics. "VCF data" is data stored in the VCF format. The variant call format stores only the variations need to be stored along with a reference genome.

The General Feature Format (GFF) stored all of the genetic data, much of which is redundant because it will be shared across the genomes. "GFF data" is data stored in the GFF format.

A "graph alignment" can include the analysis of genomic data using graphs and graph representations that are not directed acyclic graphs, such as de Bruijn graphs. For example a genome variation map graph can be used to analyze raw sequence data by graph alignment.

The term "subject", as used herein, generally refers to a specific source of genetic materials. The subject can be a biological entity. The biological entity can be a plant, animal, or microorganism, including, without limitation, bacteria, viruses, fungi, and protozoa. The subject can be an organ, tissue, or cell. A subject can be obtained in vivo or cultured in vitro. The subject can be a cell line. The subject can be propagated in culture. The subject can be disease cells. The subject can be cancer cells. The subject can be a mammal. The mammal can be a human. The term "subject" does not denote a particular age. Thus, both adult and newborn individuals are intended (e.g., adult and newborn humans) to be covered.

As used herein, the term "sample" refers to any substance containing or presumed to contain material from which genomic, proteomic, epigenomic, or metabolomic information can be obtained. Accordingly, a sample can be any substance containing or presumed to contain nucleic acids, proteins, or peptides. The sample can be a biological sample obtained from a subject. The nucleic acids can be RNA, DNA, e.g., genomic DNA, mitochondrial DNA, viral DNA, synthetic DNA, or cDNA reverse transcribed from RNA. As used herein, a "biological sample" refers to a sample of cells, tissue, or fluid isolated from a prokaryotic or eukaryotic organism, including but not limited to, for example, blood, plasma, serum, fecal matter, urine, bone marrow, bile, spinal fluid, lymph fluid, sputum, ascites, bronchial lavage fluid, synovial fluid, samples of the skin, external secretions of the skin, respiratory, intestinal, and genitourinary tracts, tears, saliva, milk, organs, biopsies, and also samples of cells, including cells from bacteria, fungi, protists, plants, and animals as well as in vitro cell culture constituents, including but not limited to, conditioned media resulting from the growth of cells and tissues in culture medium, e.g., recombinant cells, and cell components, and also samples containing nucleic acids from viruses. In some cases, the biological sample is a liquid sample. The liquid sample can be whole blood, plasma, serum, ascites, semen, cerebrospinal fluid, sweat, urine, tears, saliva, buccal sample, cavity rinse, or organ rinse. The liquid sample can be an essentially cell-free liquid sample (e.g.,cell-free fraction, plasma, serum, sweat, urine, tears, etc). In other embodiments, the biological sample is a solid biological sample, e.g., feces, hair, nail, or tissue biopsy, e.g., a tumor biopsy. A sample can also comprise in vitro cell culture constituents (including but not limited to conditioned medium resulting from the growth of cells in cell culture medium, recombinant cells and cell components). A sample can comprise or be derived from cancer cells.

"Nucleotides" can be biological molecules that can form nucleic acids. Nucleotides can have moieties that contain not only the known purine and pyrimidine bases, but also other heterocyclic bases that have been modified. Such modifications include methylated purines or pyrimidines, acylated purines or pyrimidines, alkylated riboses, or other heterocycles. In addition, the term "nucleotide" includes those moieties that contain hapten, biotin, or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the like.

"Nucleotides" can also include locked nucleic acids (LNA) or bridged nucleic acids (BNA). BNA and LNA generally refer to modified ribonucleotides wherein the ribose moiety is modified with a bridge connecting the 2' oxygen and 4' carbon. Generally, the bridge "locks" the ribose in the 3'-endo (North) conformation, which is often found in the A-form duplexes. The term "locked nucleic acid" (LNA) generally refers to a class of BNAs, where the ribose ring is "locked" with a methylene bridge connecting the 2'-O atom with the 4'-C atom. LNA nucleosides containing the six common nucleobases (T, C, G, A, U, and mC) that appear in DNA and RNA are able to form base-pairs with their complementary nucleosides according to the standard Watson-Crick base pairing rules. Accordingly, BNA and LNA nucleotides can be mixed with DNA or RNA bases in an oligonucleotide whenever desired. The locked ribose conformation enhances base stacking and backbone pre-organization. Base stacking and backbone pre-organization can give rise to an increased thermal stability (e.g., increased Tm) and discriminative power of duplexes. LNA can discriminate single base mismatches under conditions not possible with other nucleic acids.

The terms "polynucleotides", "nucleic acid", "nucleotides" and "oligonucleotides" can be used interchangeably. They can refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, the "proteome" refers to the entirety of all proteins within a living organism, a tissue, a cell, a cell compartment or a virus, or secreted or otherwise released by an organism into the environment. Unlike genomes, proteomes are dynamic: the proteins making up a cell's proteome change in response to the cell's chemical and physical environment. Proteomic data sets, which comprise sequence information about the expressed proteins in an organism can be obtained. Proteomic data sets can comprise information about post-translationally modified proteins in the proteome. Proteomic data sets can be obtained at a specific point in time. In some cases, proteomic data are generated using instruments such as a mass spectrometer and called proteomic sequences that may be further processed and assembled into sets. Proteomic data are typically archived in various repositories for future reference.

A "variant" can be an alteration in the normal sequence of a nucleic acid sequence (e.g., a gene). In some instances a genotype and corresponding phenotype is associated with a variant. In other instances there is no known function of a variant. A variant can be a single nucleotide polymorphism (SNP). A variant can be a single nucleotide variation (SNV) in, for example, protein-coding sequence. A variant can be an insertion of a plurality of nucleotides. A variant can be a deletion of a plurality of nucleotides. A variant can be a mutation. A variant can be a copy number variation (CNV). A variant can be a structural variant. A variant can be a nucleic acid deviation between two or more individuals in a populations.

The term "target polynucleotide," as use herein, generally refers to a polynucleotide of interest under study. In certain embodiments, a target polynucleotide contains one or more sequences that are of interest and under study. A target polynucleotide can comprise, for example, a genomic sequence. The target polynucleotide can comprise a target sequence whose presence, amount, and/or nucleotide sequence, or changes in these, are desired to be determined. In some instances a target polynucleotide is aligned to an alternative path. In some instances the target polynucleotide is preselected. In some instances the target polynucleotide is identified during the course of a study or as the output of a study.

The term "genome" can refer to the genetic complement of a biological organism, and the terms "genomic data" and "genomic data set" include sequence information of chromosomes, genes, or DNA of the biological organism. A genomic data set typically includes the genetic material sequenced into a plurality of sequences, called genomic sequences that may be further processed and assembled into sets. Generally, genomic data is typically archived in various repositories for future reference.

The term "genomic data," as used herein, refers to data that can be one or more of the following: the genome or exome sequence of one or more, or any combination or mixture of one or more mitochondria, cells, including eggs and sperm, tissues, neoplasms, tumors, organs, organisms, microorganisms, viruses, individuals, or cell-free DNA and further including, without limitation, nucleic acid sequence information, genotype information, gene expression information, genetic data, epigenetic information including DNA methylation, acetylation or similar DNA modification data, RNA transcription, splicing, editing or processing information, or medical, health or phenotypic data, or nutritional, dietary or environmental condition or exposure information or other attribute data of any microorganism, virus, cell, tissue, neoplasm, tumor, organ, organ system, cell-free sample (e.g. serum or media), individual or group of samples or individuals. Accordingly, the term "genomic sequence," as used herein, refers to a sequence that occurs in a genome. Because RNAs are transcribed from a genome, this term encompasses sequence that exist in the nuclear genome of an organism, as well as sequences that are present in a. cDNA copy of an RNA (e.g., an mRNA) transcribed from such a genome. "Genomic sequence" can also be a sequence that occurs on the cytoplasm or in the mitochondria.

The terms "determining," "measuring," "evaluating," "assessing," "assaying," and "analyzing" can be used interchangeably herein to refer to any form of measurement, and can include determining if an element is present or not. These terms can include both quantitative and/or qualitative determinations. Assessing may be relative or absolute. "Assessing the presence of" can include determining the amount of something present, as well as determining whether it is present or absent.

The term "genomic fragment", as used herein, can refer to a region of a genome, e.g., an animal or plant genome such as the genome of a human, monkey, rat, fish or insect or plant. A genomic fragment may or may not be adaptor ligated. A genomic fragment may be adaptor ligated (in which case it has an adaptor ligated to one or both ends of the fragment, to at least the 5' end of a molecule), or non-adaptor ligated.

The term "sequencing", as used herein, can refer to a method by which the identity of at least 10 consecutive characters (e.g., nucleotide, amino acids) are obtained. For genomic data, sequencing comprises obtaining the identity of at least 10, at least 20, at least 50, at least 100, at least 200, or at least 500 or more consecutive nucleotides of a polynucleotide. For proteomic data, sequencing comprises obtaining the identity of at least 10, at least 20, at least 50, at least 100, at least 200, or at least 500 or more consecutive amino acids of a polypeptide sequence.

The term "barcode sequence" as used herein, generally refers to a sequence of nucleotides that can encode information about an assay. In some instances barcodes are unique. A barcode sequence can encode information relating to the identity of an interrogated allele, identity of a target polynucleotide or genomic locus, identity of a sample, a subject, or any combination thereof. A barcode sequence can be a portion of a primer, a reporter probe, or both. A barcode sequence may be at the 5'-end or 3'-end of an oligonucleotide, or may be located in any region of the oligonucleotide. Barcode sequences can be non-naturally occurring, e.g. sequences which do not occur in the sample under study. In other instances naturally occurring sequences can be used as barcodes or as a part of a barcode sequence. In some instances junctions, where nucleic acids have been joined can serve as bar codes. In some instances sequencing adaptors can serve as a barcodes or as a part of barcodes. In some instances the barcodes are in excess of a target molecule, e.g. a genomic sequence of interest. In some instances a barcode is associated with a target molecule randomly or semi-randomly. In some instances a barcode is associated with a target molecule by design.

The term "mutation", as used herein, generally refers to a change of the nucleotide sequence of a genome or other genetic variation. Mutations can involve large sections of DNA. For example, copy number variations (CNVs) can involve large portions of a genome and often involve complex repetitive DNA sequences. CNVs can also encompass entire genes, many of which have a specific function ascribed to them. In some cases, mutations involve whole chromosomes (e.g., aneuploidy). Mutations can involve small sections of DNA. Examples of mutations involving small sections of DNA include, e.g., point mutations or single nucleotide polymorphisms, multiple nucleotide polymorphisms, insertions (e.g., insertion of one or more nucleotides at a locus), multiple nucleotide changes, deletions (e.g., deletion of one or more nucleotides at a locus), and inversions (e.g., reversal of a sequence of one or more nucleotides).

The term "locus", as used herein, can refer to a location of a gene, nucleotide, or sequence on a chromosome. An "allele" of a locus, as used herein, can refer to an alternative form of a nucleotide or sequence at the locus. A "wild-type allele" generally refers to an allele that has the highest frequency in a population of subjects. A "wild-type" allele generally is not associated with a disease. A "mutant allele" generally refers to an allele that has a lower frequency that a "wild-type allele" and may be associated with a disease. A "mutant allele" may not have to be associated with a disease. The term "interrogated allele" generally refers to the allele that an assay is designed to detect.

The term "single nucleotide polymorphism", or "SNP", as used herein, generally refers to a type of genomic sequence variation resulting from a single nucleotide substitution within a sequence. "SNP alleles" or "alleles of a SNP" generally refer to alternative forms of the SNP at particular locus. The term "interrogated SNP allele" generally refers to the SNP allele that an assay is designed to detect.

Methods

Although the description herein provides considerable detail with respect to genetic data and nucleotide sequences, it will be understood that the methods and systems for compression can be implemented for other data sets as well, such as proteomic, epigenomic, and metabolomic data. Accordingly when the term "genomic data" is used, the methods can be applied to other biologic sequence data such as proteomic, epigenomic, and metabolomic data when appropriate. Proteomic sequences include, without limitation, peptide molecular weights or amino acid sequences (A, K, M, R, L, U, T, V, L, S, Q, W, I, P, F, H, C, D, Y . . . ) (see FIG. 1). Peptides may be unmodified or chemically modified. Epigenetic data sets can include DNA sequences, or RNA sequences, or molecular weights of modified and unmodified peptides.

Generally, biological material extracted from either a biological or an environmental sample is processed, analyzed, and stored as biological data for research or medical purposes. Any appropriate mechanism for sequence data collection can be used according to the methods provided herein. For example, sequence data can be collected using one or more next generation sequence platforms. As used herein, the term "next generation sequencing platform" refers to DNA sequencing methodologies that share the common feature of massively parallel, high-throughput strategies, with the goal of lower costs in comparison to older sequencing methods (see, e.g., Voelkerding et al., *Clinical Chem.*, 55: 641-658, 2009; MacLean et al, *Nature Rev. Microbiol*, 7-287-296; each herein incorporated by reference in their entirety). Data collected using a next generation sequencing (NGS) platform typically include information such as sequencing reads, quality values/information, annotations, and the like. NGS methods can be broadly divided into those that typically use template amplification and those that do not. Amplification-requiring methods include commercially available platforms such as pyrosequencing commercialized by Roche as the 454 technology platforms (e.g., GS 20 and GS FLX), the Solexa platform commercialized by Illumina (e.g., HiSeq X Ten), and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos Biosciences, and emerging platforms commercialized by VisiGen, Oxford Nanopore Technologies Ltd. (Mini-ION and PrometlON), Life Technologies/Ion Torrent, and Pacific Biosciences, respectively.

Platforms for sequencing by synthesis are available from, e.g., Illumina, 454 Life Sciences, Helicos Biosciences, and Qiagen. Illumina platforms can include, e.g., Illumina's Solexa platform, Illumina's Genome Analyzer, and are described in Gudmundsson et al (Nat. Genet. 2009 41:1122-6), Out et al (Hum. Mutat. 2009 30:1703-12) and Turner (Nat. Methods 2009 6:315-6), U.S. Patent Application Pub nos. US2008/0160580 and US2008/0286795, U.S. Pat. Nos. 6,306,597; 7,115,400; and 7,232,656. 454 Life Science platforms include, e.g., the GS Flex and GS Junior, and are described in U.S. Pat. No. 7,323,305. Platforms from Helicos Biosciences include the True Single Molecule Sequencing platform. Platforms for ion semiconductor sequencing include, e.g., the Ion Torrent Personal Genome Machine (PGM) and are described in U.S. Pat. No. 7,948,015. Platforms for pryosequencing include the GS Flex 454 system and are described in U.S. Pat. Nos. 7,211,390; 7,244,559; 7,264,929. Platforms and methods for sequencing by ligation include, e.g., the SOLiD sequencing platform and are described in U.S. Pat. No. 5,750,341. Platforms for single-molecule sequencing include the SMRT system from Pacific Bioscience and the Helicos True Single Molecule Sequencing platform.

While the automated Sanger method is considered as a 'first generation' technology, Sanger sequencing including the automated Sanger sequencing, can also be employed by the method of the invention. Additional sequencing methods that comprise the use of developing nucleic acid imaging technologies (e.g., atomic force microscopy (AFM) or transmission electron microscopy (TEM)) are also encompassed by the method of the invention. Exemplary sequencing technologies are described below.

In some cases, next generation sequencing technology utilizes the Ion Torrent sequencing platform, which pairs semiconductor technology with a sequencing chemistry to directly translate chemically encoded information (A, C, G, T) into digital information (0, 1) on a semiconductor chip. Without wishing to be bound by theory, when a nucleotide is incorporated into a strand of DNA by a DNA polymerase, a hydrogen ion is released as a byproduct. The Ion Torrent platform detects the release of the hydrogen atom as a change in pH. A detected change in pH can be used to indicate nucleotide incorporation. The Ion Torrent platform comprises a high-density array of micro-machined wells to perform this biochemical process in a massively parallel way. Each well holds a different library member, which may be clonally amplified. Beneath the wells is an ion-sensitive layer and beneath that an ion sensor. The platform sequentially floods the array with one nucleotide after another. When a nucleotide, for example a C, is added to a DNA template and is then incorporated into a strand of DNA, a hydrogen ion will be released. The charge from that ion will change the pH of the solution, which can be identified by Ion Torrent's ion sensor. If the nucleotide is not incorporated, no voltage change will be recorded and no base will be called. If there are two identical bases on the DNA strand, the voltage will be double, and the chip will record two identical bases called. Direct identification allows recordation of nucleotide incorporation in seconds. Library preparation for the Ion Torrent platform generally involves ligation of two distinct adaptors at both ends of a DNA fragment.

The next generation sequencing technology can utilize an Illumina sequencing platform, which generally employs cluster amplification of library members onto a flow cell and a sequencing-by-synthesis approach. Cluster-amplified library members are subjected to repeated cycles of polymerase-directed single base extension. Single-base extension can involve incorporation of reversible-terminator dNTPs, each dNTP labeled with a different removable fluorophore. The reversible-terminator dNTPs are generally 3' modified to prevent further extension by the polymerase. After incorporation, the incorporated nucleotide can be identified by fluorescence imaging. Following fluorescence imaging, the fluorophore can be removed and the 3' modification can be removed resulting in a 3' hydroxyl group, thereby allowing another cycle of single base extension. Library preparation for the Illumina platform generally involves ligation of two distinct adaptors at both ends of a DNA fragment.

The next generation sequencing technology that is used in the method of the invention can be the Helicos True Single Molecule Sequencing (tSMS), which can employ sequencing-by-synthesis technology. In the tSMS technique, a polyA adaptor can be ligated to the 3' end of DNA fragments. The adapted fragments can be hybridized to poly-T oligonucleotides immobilized on the tSMS flow cell. The library members can be immobilized onto the flow cell at a density of about 100 million templates/cm$^2$. The flow cell can be then loaded into an instrument, e.g., HELISCOPE™ sequencer, and a laser can illuminate the surface of the flow cell, revealing the position of each template. A CCD camera can map the position of the templates on the flow cell surface. The library members can be subjected to repeated cycles of polymerase-directed single base extension. The sequencing reaction begins by introducing a DNA polymerase and a fluorescently labeled nucleotide. The polymerase can incorporate the labeled nucleotides to the primer in a template directed manner. The polymerase and unincorporated nucleotides can be removed. The templates that have directed incorporation of the fluorescently labeled nucleotide can be discerned by imaging the flow cell surface. After imaging, a cleavage step can remove the fluorescent label, and the process can be repeated with other fluorescently labeled nucleotides until a desired read length is achieved. Sequence information can be collected with each nucleotide addition step.

The next generation sequencing technology can utilize a 454 sequencing platform (Roche) (e.g., as described in Margulies, M. et al. *Nature* 437:376-380 [2005]). 454 sequencing generally involves two steps. In a first step, DNA can be sheared into fragments. The fragments can be blunt-ended. Oligonucleotide adaptors can be ligated to the ends of the fragments. The adaptors generally serve as primers for amplification and sequencing of the fragments. At least one adaptor can comprise a capture reagent, e.g., a biotin. The fragments can be attached to DNA capture beads, e.g., streptavidin-coated beads. The fragments attached to the beads can be PCR amplified within droplets of an oil-water emulsion, resulting in multiple copies of clonally amplified DNA fragments on each bead. In a second step, the beads can be captured in wells, which can be pico-liter sized. Pyrosequencing can be performed on each DNA fragment in parallel. Pyrosequencing generally detects release of pyrophosphate (PPi) upon nucleotide incorporation. PPi can be converted to ATP by ATP sulfurylase in the presence of adenosine 5' phosphosulfate. Luciferase can use ATP to convert luciferin to oxyluciferin, thereby generating a light signal that is detected. A detected light signal can be used to identify the incorporated nucleotide.

The next generation sequencing technology can utilize a SOLiD™ technology (Applied Biosystems). The SOLiD platform generally utilizes a sequencing-by-ligation approach. Library preparation for use with a SOLiD platform generally comprises ligation of adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations can be prepared in microreactors containing beads, primers, template, and PCR components. Following PCR, the templates can be denatured. Beads can be enriched for beads with extended templates. Templates on the selected beads can be subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide can be removed and the process can then be repeated.

The next generation sequencing technology can utilize a single molecule, real-time (SMRT™) sequencing platform (Pacific Biosciences). In SMRT sequencing, the continuous incorporation of dye-labeled nucleotides can be imaged during DNA synthesis. Single DNA polymerase molecules can be attached to the bottom surface of individual zero-mode wavelength identifiers (ZMW identifiers) that obtain sequence information while phospholinked nucleotides are being incorporated into the growing primer strand. A ZMW generally refers to a confinement structure which enables observation of incorporation of a single nucleotide by DNA polymerase against a background of fluorescent nucleotides that rapidly diffuse in an out of the ZMW on a microsecond scale. By contrast, incorporation of a nucleotide generally occurs on a milliseconds timescale. During this time, the fluorescent label can be excited to produce a fluorescent signal, which is detected. Detection of the fluorescent signal can be used to generate sequence information. The fluorophore can then be removed, and the process repeated. Library preparation for the SMRT platform generally involves ligation of hairpin adaptors to the ends of DNA fragments.

The next generation sequencing technology can utilize nanopore sequencing (e.g., as described in Soni GV and Meller A. *Clin Chem* 53: 1996-2001 (2007)). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore can be a small hole, of the order of 1 nanometer in diameter Immersion of a nanopore in a conducting fluid and application of a potential (voltage) across can result in a slight electrical current due to conduction of ions through the nanopore. The amount of current which flows is sensitive to the size and shape of the nanopore and to occlusion by, e.g., a DNA molecule. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

The next generation sequencing technology can utilize a chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

The next generation sequencing technology can utilize transmission electron microscopy (TEM). The method, termed Individual Molecule Placement Rapid Nano Transfer (IMPRNT), generally comprises single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

The method can utilize sequencing by hybridization (SBH). SBH generally comprises contacting a plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be identified and used to identify the plurality of polynucleotide sequences within the sample. The length of the sequence read can vary depending on the particular sequencing technology utilized. NGS platforms can provide sequence reads that vary in size from tens to hundreds, or thousands of base pairs, or even tens or hundreds of thousands of base pairs. In some embodiments of the method described herein, the sequence reads are about 20 bases long, about 25 bases long, about 30 bases long, about 35 bases long, about 40 bases long, about 45 bases long, about 50 bases long, about 55 bases long, about 60 bases long, about 65 bases long, about 70 bases long, about 75 bases long, about 80 bases long, about 85 bases long, about 90 bases long, about 95 bases long, about 100 bases long, about 110 bases long, about 120 bases long, about 130, about 140 bases long, about 150 bases long, about 200 bases long, about 250 bases long, about 300 bases long, about 350 bases long, about 400 bases long, about 450 bases long, about 500 bases long, about 600 bases long, about 700 bases long, about 800 bases long, about 900 bases long, about 1000 bases long, or more than 1000 bases long.

In some embodiments, partial sequencing of DNA fragments present in the sample can be performed.

In order to increase the efficiency of the repositories in storing sequence data and also to reduce costs related to storage, genomic and proteomic sequence data may be compressed before being stored. Conventional compression techniques employed by sequence repositories or databases are based on compression techniques that are generally used for compression of text files, and are thus unable to optimally compress the genomic data. Disclosed herein are optimized systems and methods for storing and analyzing these data.

The systems and methods disclosed herein can utilize the identification of repeated patterns of known bases prevalent within the genomic sequences. The identification of these repeated patterns can be used as a step in larger compression scheme, wherein the compression is not wholly based on this step. Known bases for genomic data include primary characters 'A', 'T', 'G', and 'C', which correspond to four nucleotide bases, adenine (A), thymine (T), guanine (G), and cytosine (C).

In addition to known bases or primary characters, sequence data may alternatively or additionally comprise intermediary data, for example, secondary characters or symbols that represent gaps of indeterminate length. The systems and methods disclosed herein can, in some instances, accurately identify or handle such characters. This can allow accurate compression/decompression of the genomic sequence. In some instances this results in lossless compression/decompression of the genomic information.

Certain known algorithmic implementations specialized for genomic data compression may have high compression and/or decompression time and memory requirements, thus increasing the processing costs. An inefficient compression/decompression of the genomic data in terms of time taken may additionally affect research by hindering quick and efficient storage, retrieval, and transmission of the genomic data. Disclosed herein are methods and systems which improve the efficiency of the compression/decompression, thus allowing for quick and efficient storage, retrieval, and transmission of the genomic data.

Referring particularly now to FIG. 2, an implementation of a data compression system is shown. In a first step, a sample containing or expected to contain data of biological origin is obtained from a subject. Examples of data include those of genomic origin (DNA-derived or RNA-derived), or proteomic origin (mass spectrometry-derived). In some cases the data may be of genomic and proteomic, as in the case of epigenetic data. Genomic data generally comprises a plurality of genetic sequences. A genetic sequence typically includes data in the form of primary characters, and is preceded by a header section having information about the genetic sequence. For instance, data in nucleotide sequences may be represented in the form of primary characters 'A', 'T', 'G', and 'C', which correspond to four nucleotide bases, adenine (A), thymine (T), guanine (G), and cytosine (C), while the header information includes data, such as an ID of the project for which the nucleotide sequence is generated and sequence ordering. Further, genomic sequences may also include secondary characters, such as non-ATGC characters, like 'Y', 'W', 'M', 'K', 'B', 'V', 'D', 'N', 'H', 'R', and 'S' in the case of nucleotide sequences. In some embodiments, the secondary characters, such as 'H', 'N' or '-' may be removed to facilitate efficient compression. The modified genomic data thus includes only a plurality of the primary characters. For instance, the modified genomic data for nucleotide sequences may only include a plurality of primary characters A', 'T', 'G', and 'C.

In some cases, data may comprise proteomic data having a plurality of protein or peptide sequences. A protein sequence is typically a sequence of letters from a 20-letter alphabet of single-letter characters by which the amino acids may be represented in databases. Amino acids also can be represented by standard 3-letter abbreviations. The standard International Union of Pure and Applied Chemistry (IUPAC) one-letter codes for amino acids are provided in FIG. 1.

Genomic or proteomic data is received by a sequence module. In one non-limiting example, data collection comprises a sequencing reaction performed using a Illumina HiSeq2500. When run at rapid run mode and set to produce 2×100 reads, the reaction generates 100 billion bases (100 gigabases). The sequencing data itself occupies 100 gigabytes, while the complete processing data will exceed 200 gigabytes as it pertains to read quality, and header data. This data throughput is produced in the order of 27 hours. In other run modes the HiSeq2500 can be run to generate up to 1 trillion nucleotides by producing 2×125 reads in its high output run mode. The complete FASTQ data in this case will be exceed 2 terabytes (TB), while the raw sequencing data will be 1 TB (the equivalent of 1,024 gigabytes).

Transfer of data can be received via a plurality of transfer protocols using a local area network, a wide area network, or a combination of these. In some embodiments, the sequencer will be accessed directly to the computing device. Access to the sequencing data will rely on the speed of the hard drive. In the case of hard disk drive (HDD) the rate will be 50-300 megabases/second. In the case of solid state drive (SSD), the rate will be 400-10,000 megabases/second. In other embodiments, the read data will be transferred directly in RAM (12,000 megabases/second).

Referring to FIG. 2, the data compression system 100 can be implemented in systems that include, but are not limited to, mainframe computers, desktop computers, hand-held devices, multiprocessor systems, personal digital assistants (PDAs), laptops, network computers, cloud servers, minicomputers, implantable devices, and the like. In some instances parts or all of the data compression system is integrated into a sequencing device. In some instances a sequencing device outputs data compressed as described herein. In one non-limiting example, the data compression system 100 includes interface(s) 102, one or more processor(s) 104, and a memory 106 coupled to the processor(s) 104.

The interfaces 102 may include a variety of software and hardware interfaces, for example, interfaces for peripheral device(s), such as a keyboard, a mouse, an external memory, and a printer. In some instances the peripheral device is a sequencer. In some instances the data compression system interfaces with multiple sequencers running in parallel. Further, the interfaces 102 may enable the system 100 to communicate with other devices, such as web servers and external databases. The interfaces 102 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 102 may include one or more ports for connecting a number of computing systems with one another or to another server computer.

The processor(s) 104 can be a single processing unit or a number of units. The processor 104 may be implemented as one or more microprocessors, microcomputers, microcontrollers, digital signal processors, central processing units, state machines, logic circuitries, and/or any devices that manipulate signals based on operational instructions. Among other capabilities, the processor 104 is configured to fetch and execute computer-readable instructions and data stored in the memory 106.

The memory 106 may include any computer-readable medium known in the art including, for example, volatile memory such as static random access memory (SRAM) and dynamic random access memory (DRAM), and/or non-volatile memory, such as read only memory (ROM), erasable programmable ROM, flash memories, hard disks, optical disks, and magnetic tapes. The memory 106 may be in communication with a sequencer 108 and a compression module 110.

In one non-limiting example, the compression module 110 may be configured to compress the genome sequencing data 112 by up to about 75% for transmission to the database 106 to be stored and/or to the processor 104 for further processing. The system 100 provides reduction of data transmission by modifying reads to a 2-bit representation without ideal compression. Genome read data 112 (i.e., A, C, G, T), when it is not compressed, is transmitted using 8 bits (i.e., 1 byte) per letter. As previously described, there are other cases where an extra symbol (e.g., 'N'), is included in the sequence data 112 since the genome data can contain errors and an 'N' is added where there is not enough information to distinguish the base pairs.

The sequence data 112 can be transferred to a data compression module 110 that is configured to assigning a binary number to each of the primary characters in the sequence, beginning from 0. The compression module 110 may further be configured to assign a 2-bit representation to each of the base pairs in the sequence. For example, the primary character 'A' may be represented as 00; the primary character 'C' may be represented as 01; the primary character 'G' may be represented as 10; and the primary character 'T' may be represented as 11. As the data 112 is transmitted in bytes (8-bits), it is then possible to transmit four base pairs per byte. For instance, '10000111', when decoded, represents GACT, and a corresponding compression of 75% of the data stream. In some embodiments, more complicated compression methods (e.g., Huffman coding, order-0 arithmetic coding, etc.) applied by the compression module 110 can reach similar rates in some cases.

In comparison to the data types described above, in another non-limiting example, the genomic and proteomic data may be 1-byte data types configured to fit four bases, 2-byte data types (e.g., short integer type) configured to fit eight bases, or 4-byte data types (e.g., basic integer type) configured to fit sixteen bases.

In other embodiments, the secondary characters (e.g., 'N') may be included in the sequence data 112. As a result, the bit space may increased to 3, for example, resulting in approximately 50% compression. Alternatively, the secondary characters (e.g., 'N') may be removed from the sequence data 112. Thus, the sequence data may then be stored with respect to its base, and then transmit its positions. In another example, the compression module 110 may provide variable lossless compression schemes that map symbols to different encodings. While it may shorten some files, it necessarily makes others larger. Thus, regardless of the size of the data, about a 25% reduction may be obtained.

When the secondary characters (e.g., 'N') are removed from the sequence data 112, the secondary characters may simply be extracted and the corresponding quantity and positions of the secondary characters may be stored in the database 106 as shown, for example, in FIG. 2. In one non-limiting example, the data corresponding to the quantity and positions of secondary characters may be stored in 2-byte data types, where each secondary character is between 2-4 bytes. Additionally, or alternatively, the data corresponding to the secondary characters may be stored in one byte data types, two byte data types, four byte data types, 8 byte data types, 16 byte data types, 32 byte data types, 64 byte data types, or more than 64 byte data types. Once the secondary characters are extracted from the sequence data 112, the compression module 110 may compress of the genome read data (i.e., A, C, G, T). Thus, compression may be between about 25% and 50% of the data.

In the embodiment above described, the quantity of secondary characters may not exceed about 5% of the sequence. Thus, for a sequence of genomic data typically having approximately 101 bytes, the data is now saved in approximately 35 bytes (i.e., 25 bytes for reads, 2 bytes for quantity of secondary characters, and 8 bytes for the position of each secondary character).

Figure 3:
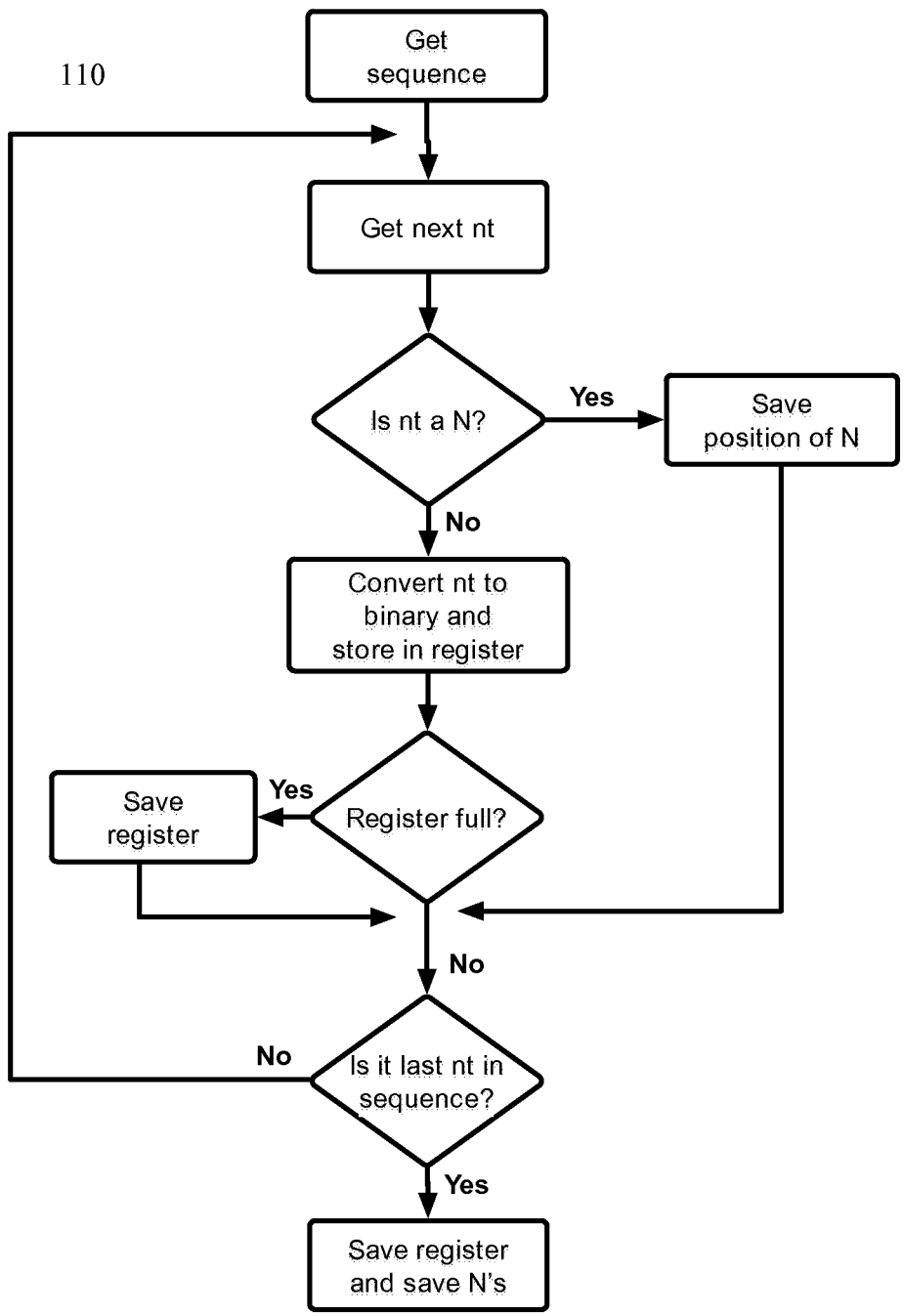
FIG. 3 illustrates a system for compression with unknown sequence information 'N.' The user obtains a sequence. Each nucleotide (nt) is determined to be a primary or secondary ('N') character. If identified as a secondary character/N, the nt is saved separately. If identified as a primary character, the nt is converted to its binary (bit) equivalent and stored in the register. If the register is full, then it is saved. If it is the last nucleotide, then the register is saved and the list of N's is also saved.

As shown in FIG. 3, secondary characters can be removed. After obtaining a sequence composed of nucleotides, each nucleotide is read. If the nucleotide is a secondary character (regarded as 'N'), then the position of N is saved within the sequence and reading continues along the sequence. If the read is not an N, then the nucleotide is converted to its binary representation (as shown in FIG. 3, but other embodiments could have a different mapping) and stored in a register according to certain mathematical or computational operations. If the register is full save it and read the next sequence element until the last element of the sequence is reached. If the register is 1 byte, each register can hold 4 nucleotides, if the register is 2 bytes, each register can hold 8 nucleotides, etc.

As described above, the data 112 may also include proteomic data having a plurality of amino acid residues (e.g., including unmodified, non-proteogenic, and modified residues) that are received by the compression module 110 for compression as well as modified amino acids like include methylations, acetylations for example, In one example, the data compression system 100 may be configured to map residue space in five bits (i.e., $2^5=32$). Using 4-byte data types (i.e., basic integer type) for the proteomic data, the data compression system 100 can pack six bases, in contrast to one byte per base if not encoded. Thus, in these embodiments, the data compression system 100 may compress the proteomic data by up to approximately 20%.

Alternatively, the data compression system may save a plurality of residues in the base sequence. Thus, in the 15-base sequence having a five-nucleotide sequence compression is approximately 20%. The 20% compression may be due to the 15-base sequence being able to fit into a 4-byte data type (i.e., basic integer type).

FIG. 3 shows an example diagram for the above described compression process, performed by the compression module 110. Depending on the requirements of a text-based format (e.g., a FASTQ file) for storing the sequence data 112 and corresponding quality scores, a shallow or deep compression process may be performed. If a shallow or expedite compression is required, the compression module 110 may be configured to mix compression methods depending on the different parts of information that describe the reads form the sequencer 108. Alternatively, if a deep or whole compression is required, primarily for storage purposes, the compression module may be configured to perform a mixture of compression methods depending on the different parts of information.

In contrast to conventional compression systems for genomic and proteomic data, the data compression system 100 may be a fixed system, not a variable system. Additionally, the genomic data and proteomic data may have a separate, fixed encoding scheme, and quality data may have a separate fixed encoding scheme from the genomic data and proteomic data. Thus, the compression module 110 may be configured to transmit two groups of 4-bits (i.e., one group for the fixed genomic data and proteomic data, and one group for the quality data).

Figure 4:
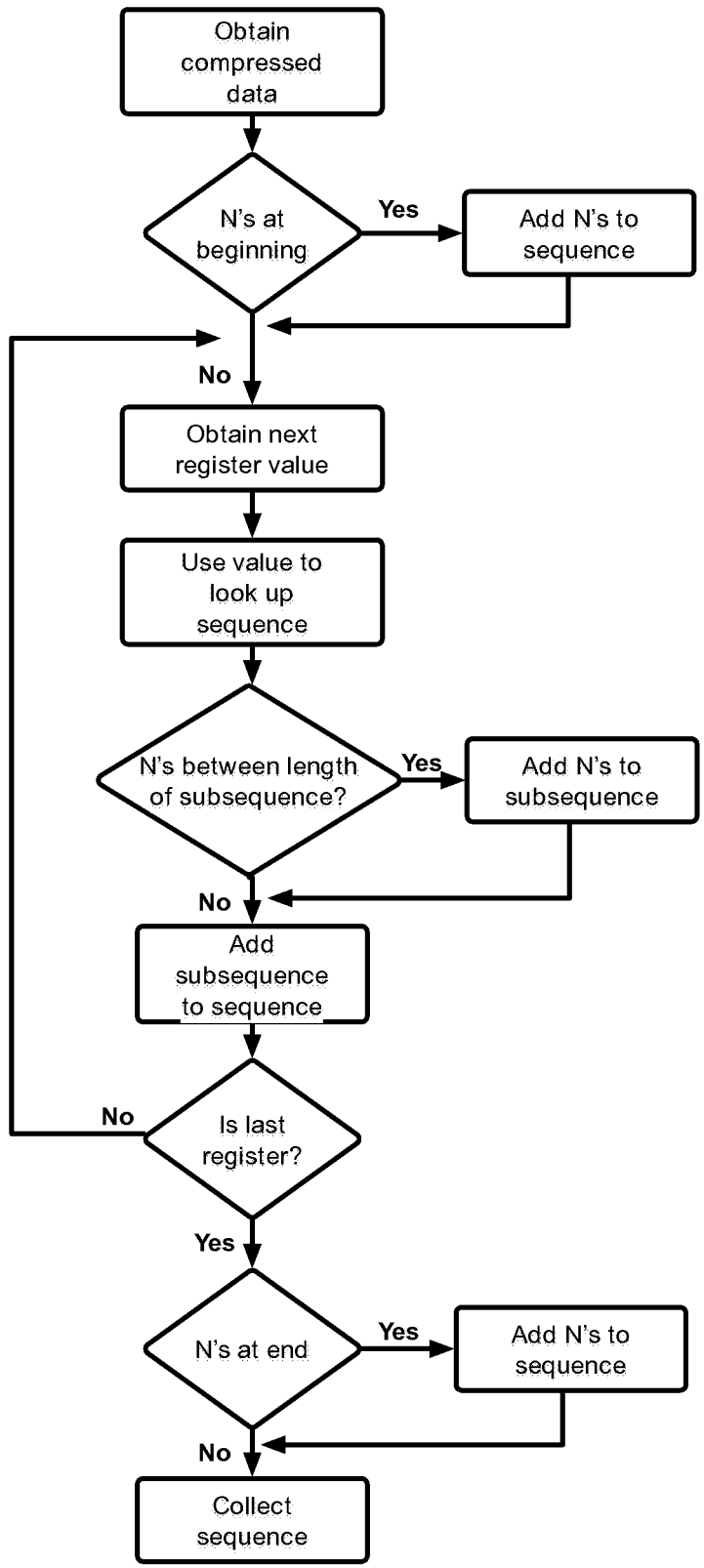
FIG. 4 illustrates a system for decompression with unknown sequence information 'N.' The user obtains the compressed data and determines if the compressed data has secondary characters ('N') at the beginning. If there are secondary characters, those are stored in the sequence. If not, then the next set of nucleotides are obtained from the register lookup. If there are any secondary characters in between the subsequence, then those are added. Afterwards the subsequence is saved to the sequence. If this is not the last register, the next register value is obtained and the previous steps are repeated. If it is the last register, it is determined whether there are secondary characters at the end. If so, those are added to the sequence. The whole sequence is collected at the last point.

To decompress compressed data, the registers are read and converted to sequence information. In some cases, the registers are converted sequentially (FIG. 4). To convert a number to sequence, it is possible to perform the reverse procedure as in compression: read bits 7-8 to extract the first nucleotide, bits 5-6 to extract the second nucleotide, bit 3-4 to extract the third nucleotide and bits 1-2 to extract the fourth nucleotide in the register. In other embodiments, the nucleotides can be stored in a different permutation or reversible permutation.

In other cases, conversion of the register to sequence information is done using a lookup table. For a 1 byte register, one can translate its numerical component to its 4 nucleotide equivalent (see Table 1). For cases in which the compressed data only used 3, 2, or 1 nucleotide, a similar lookup table can be used (see Tables 2-4, respectively).

TABLE 1

Sample Lookup Table of 1 Byte Register for 4 Nucleotides

| Register | Substring |
|---|---|
| 0 | AAAA |
| 1 | AAAC |
| 2 | AAAG |
| 3 | AAAT |
| 4 | AACA |
| 5 | AACC |
| 6 | AACG |
| 7 | AACT |
| 8 | AAGA |
| 9 | AAGC |
| 10 | AAGG |
| 11 | AAGT |
| 12 | AATA |
| 13 | AATC |
| 14 | AATG |
| 15 | AATT |
| 16 | ACAA |
| 17 | ACAC |
| 18 | ACAG |
| 19 | ACAT |
| 20 | ACCA |
| 21 | ACCC |
| 22 | ACCG |
| 23 | ACCT |
| 24 | ACGA |
| 25 | ACGC |
| 26 | ACGG |
| 27 | ACGT |
| 28 | ACTA |
| 29 | ACTC |
| 30 | ACTG |
| 31 | ACTT |
| 32 | AGAA |
| 33 | AGAC |
| 34 | AGAG |
| 35 | AGAT |
| 36 | AGCA |
| 37 | AGCC |

TABLE 1-continued

Sample Lookup Table of 1 Byte Register for 4 Nucleotides

| Register | Substring |
|---|---|
| 38 | AGCG |
| 39 | AGCT |
| 40 | AGGA |
| 41 | AGGC |
| 42 | AGGG |
| 43 | AGGT |
| 44 | AGTA |
| 45 | AGTC |
| 46 | AGTG |
| 47 | AGTT |
| 48 | ATAA |
| 49 | ATAC |
| 50 | ATAG |
| 51 | ATAT |
| 52 | ATCA |
| 53 | ATCC |
| 54 | ATCG |
| 55 | ATCT |
| 56 | ATGA |
| 57 | ATGC |
| 58 | ATGG |
| 59 | ATGT |
| 60 | ATTA |
| 61 | ATTC |
| 62 | ATTG |
| 63 | ATTT |
| 64 | CAAA |
| 65 | CAAC |
| 66 | CAAG |
| 67 | CAAT |
| 68 | CACA |
| 69 | CACC |
| 70 | CACG |
| 71 | CACT |
| 72 | CAGA |
| 73 | CAGC |
| 74 | CAGG |

TABLE 1-continued

Sample Lookup Table of 1 Byte Register for 4 Nucleotides

| Register | Substring |
|---|---|
| 75 | CAGT |
| 76 | CATA |
| 77 | CATC |
| 78 | CATG |
| 79 | CATT |
| 80 | CCAA |
| 81 | CCAC |
| 82 | CCAG |
| 83 | CCAT |
| 84 | CCCA |
| 85 | CCCC |
| 86 | CCCG |
| 87 | CCCT |
| 88 | CCGA |
| 89 | CCGC |
| 90 | CCGG |
| 91 | CCGT |
| 92 | CCTA |
| 93 | CCTC |
| 94 | CCTG |
| 95 | CCTT |
| 96 | CGAA |
| 97 | CGAC |
| 98 | CGAG |
| 99 | CGAT |
| 100 | CGCA |
| 101 | CGCC |
| 102 | CGCG |
| 103 | CGCT |
| 104 | CGGA |
| 105 | CGGC |
| 106 | CGGG |
| 107 | CGGT |
| 108 | CGTA |
| 109 | CGTC |
| 110 | CGTG |
| 111 | CGTT |
| 112 | CTAA |
| 113 | CTAC |
| 114 | CTAG |
| 115 | CTAT |
| 116 | CTCA |
| 117 | CTCC |
| 118 | CTCG |
| 119 | CTCT |
| 120 | CTGA |
| 121 | CTGC |
| 122 | CTGG |
| 123 | CTGT |
| 124 | CTTA |
| 125 | CTTC |
| 126 | CTTG |
| 127 | CTTT |
| 128 | GAAA |
| 129 | GAAC |
| 130 | GAAG |
| 131 | GAAT |
| 132 | GACA |
| 133 | GACC |
| 134 | GACG |
| 135 | GACT |
| 136 | GAGA |
| 137 | GAGC |
| 138 | GAGG |
| 139 | GAGT |
| 140 | GATA |
| 141 | GATC |
| 142 | GATG |
| 143 | GATT |
| 144 | GCAA |
| 145 | GCAC |
| 146 | GCAG |
| 147 | GCAT |
| 148 | GCCA |
| 149 | GCCC |

TABLE 1-continued

Sample Lookup Table of 1 Byte Register for 4 Nucleotides

| Register | Substring |
|---|---|
| 150 | GCCG |
| 151 | GCCT |
| 152 | GCGA |
| 153 | GCGC |
| 154 | GCGG |
| 155 | GCGT |
| 156 | GCTA |
| 157 | GCTC |
| 158 | GCTG |
| 159 | GCTT |
| 160 | GGAA |
| 161 | GGAC |
| 162 | GGAG |
| 163 | GGAT |
| 164 | GGCA |
| 165 | GGCC |
| 166 | GGCG |
| 167 | GGCT |
| 168 | GGGA |
| 169 | GGGC |
| 170 | GGGG |
| 171 | GGGT |
| 172 | GGTA |
| 173 | GGTC |
| 174 | GGTG |
| 175 | GGTT |
| 176 | GTAA |
| 177 | GTAC |
| 178 | GTAG |
| 179 | GTAT |
| 180 | GTCA |
| 181 | GTCC |
| 182 | GTCG |
| 183 | GTCT |
| 184 | GTGA |
| 185 | GTGC |
| 186 | GTGG |
| 187 | GTGT |
| 188 | GTTA |
| 189 | GTTC |
| 190 | GTTG |
| 191 | GTTT |
| 192 | TAAA |
| 193 | TAAC |
| 194 | TAAG |
| 195 | TAAT |
| 196 | TACA |
| 197 | TACC |
| 198 | TACG |
| 199 | TACT |
| 200 | TAGA |
| 201 | TAGC |
| 202 | TAGG |
| 203 | TAGT |
| 204 | TATA |
| 205 | TATC |
| 206 | TATG |
| 207 | TATT |
| 208 | TCAA |
| 209 | TCAC |
| 210 | TCAG |
| 211 | TCAT |
| 212 | TCCA |
| 213 | TCCC |
| 214 | TCCG |
| 215 | TCCT |
| 216 | TCGA |
| 217 | TCGC |
| 218 | TCGG |
| 219 | TCGT |
| 220 | TCTA |
| 221 | TCTC |
| 222 | TCTG |
| 223 | TCTT |
| 224 | TGAA |

TABLE 1-continued

Sample Lookup Table of 1 Byte Register for 4 Nucleotides

| Register | Substring |
|---|---|
| 225 | TGAC |
| 226 | TGAG |
| 227 | TGAT |
| 228 | TGCA |
| 229 | TGCC |
| 230 | TGCG |
| 231 | TGCT |
| 232 | TGGA |
| 233 | TGGC |
| 234 | TGGG |
| 235 | TGGT |
| 236 | TGTA |
| 237 | TGTC |
| 238 | TGTG |
| 239 | TGTT |
| 240 | TTAA |
| 241 | TTAC |
| 242 | TTAG |
| 243 | TTAT |
| 244 | TTCA |
| 245 | TTCC |
| 246 | TTCG |
| 247 | TTCT |
| 248 | TTGA |
| 249 | TTGC |
| 250 | TTGG |
| 251 | TTGT |
| 252 | TTTA |
| 253 | TTTC |
| 254 | TTTG |
| 255 | TTTT |

TABLE 2

Sample Lookup Table of 1 Byte Register for 3 Nucleotides

| Register | Substring |
|---|---|
| 0 | AAA |
| 1 | AAC |
| 2 | AAG |
| 3 | AAT |
| 4 | ACA |
| 5 | ACC |
| 6 | ACG |
| 7 | ACT |
| 8 | AGA |
| 9 | AGC |
| 10 | AGG |
| 11 | AGT |
| 12 | ATA |
| 13 | ATC |
| 14 | ATG |
| 15 | ATT |
| 16 | CAA |
| 17 | CAC |
| 18 | CAG |
| 19 | CAT |
| 20 | CCA |
| 21 | CCC |
| 22 | CCG |
| 23 | CCT |
| 24 | CGA |
| 25 | CGC |
| 26 | CGG |
| 27 | CGT |
| 28 | CTA |
| 29 | CTC |
| 30 | CTG |
| 31 | CTT |
| 32 | GAA |
| 33 | GAC |
| 34 | GAG |
| 35 | GAT |
| 36 | GCA |
| 37 | GCC |
| 38 | GCG |

TABLE 2-continued

Sample Lookup Table of 1 Byte Register for 3 Nucleotides

| Register | Substring |
|---|---|
| 39 | GCT |
| 40 | GGA |
| 41 | GGC |
| 42 | GGG |
| 43 | GGT |
| 44 | GTA |
| 45 | GTC |
| 46 | GTG |
| 47 | GTT |
| 48 | TAA |
| 49 | TAC |
| 50 | TAG |
| 51 | TAT |
| 52 | TCA |
| 53 | TCC |
| 54 | TCG |
| 55 | TCT |
| 56 | TGA |
| 57 | TGC |
| 58 | TGG |
| 59 | TGT |
| 60 | TTA |
| 61 | TTC |
| 62 | TTG |
| 63 | TTT |

TABLE 3

Sample Lookup Table of 1 Byte Register for 2 Nucleotides

| Register | Substring |
|---|---|
| 0 | AA |
| 1 | AC |
| 2 | AG |
| 3 | AT |
| 4 | CA |
| 5 | CC |
| 6 | CG |
| 7 | CT |
| 8 | GA |
| 9 | GC |
| 10 | GG |
| 11 | GT |
| 12 | TA |
| 13 | TC |
| 14 | TG |
| 15 | TT |

TABLE 4

Sample Lookup Table of 1 Byte Register for 1 Nucleotide

| Register | Substring |
|---|---|
| 0 | A |
| 1 | C |
| 2 | G |
| 3 | T |

In this non-limiting example, the relationship between the register and the sub-sequence is given by for instance CTTA:

$$\varphi(CTTA)=4^3\varphi(C)+4^2\varphi(T)+4^0\varphi(A)$$

$$\varphi(CTTA)=64*1+16*3+4*3+0$$

$$\varphi(CTTA)=124$$

In other embodiments, the formula to generate these mappings could be any possible permutations and reversible permutations.

In other embodiments, one can also begin by analyzing if there are secondary characters at the beginning of the string (see FIG. 4). In other embodiments as the string converter is being run, one can find if there are N's within the range of the substring. Any N's remaining after the last register is filled out can be added.

The binary representation can be stored in registers. The first element is saved in the first two bits of the register, the second in the third and fourth, the third in the fifth and sixth bit, and the fourth element is saved in the seventh and eighth bit. In other embodiments, the nucleotides can be stored in a different order. In some cases, the position of the secondary characters can be saved on a list of 1 byte characters if the length of the string is less than 256 characters long. In other embodiments each element may be stored in 2 bytes, 4 bytes, etc. In other embodiments, the first element could be 2 bytes long, but the rest could be 1 byte long if the difference between them is smaller than 256 by using delta-encoding. In other cases, the number of bytes could be variable for each element.

In another aspect, provided herein are compression methods and systems wherein the resulting compressed data is expected to have a particular error rate. As used herein, the term "error" refers to an unintended change (relative to the original data) that occurs during writing, reading, storage, transmission, or processing of the data. The term "error rate" refers to the rate at which such an error (e.g., a read or write error) occurs for a given amount of data. For a hard disk drive (HDD), one read or write error is generally expected every $10^{14}$ bits. Uncompressed genomic data comprises 1 base for every 8 bits. Accordingly, one read or write error would be expected in $1.25 \times 10^{13}$ bases of processed, uncompressed data. This error rate corresponds to one error per 3906 whole genomes (or 1× coverage) of processed, uncompressed genomic data. Genomic data compressed according to the methods provided herein can comprise 4 bases for every 8 bits. Therefore, one read or write error would be expected in $5 \times 10^{13}$ bases of processed, compressed data. This corresponds to one error per 15,625 whole genomes of processed, compressed data.

For a solid state drive (SSD), one read or write error is generally expected every $10^{16}$ bits. Since this is error rate is 100 times less than that of HDD, one error would be expected in about $1.25 \times 10^{13}$ bases. This corresponds to 1 error per 390,625 whole genomes of processed, uncompressed genomic data). One error would be expected in about $5 \times 10^{15}$ bases, corresponding to 1 error per 1,562,500 whole genomes of genomic data compressed according to a method provided herein.

In an exemplary embodiment, the compression method comprises receiving at least one genomic data set into a compression module configured to encode genomic data; generating, using an encoding scheme on the compression module, a compressed data set; and transferring the compressed data set to a computer memory, where, of the bit storing genomic data, the computer memory has an average error rate between one error (e.g., read error or write error) per $10^{12}$ bases to one error per $10^{17}$ bases (e.g., one error per $10^{12}$, per $10^{13}$, per $10^{14}$, per $10^{15}$, per $10^{16}$, or per $10^{17}$ bases) of processed, compressed genomic data.

Of the bits storing genomic data, a hard disk drive can have an average error rate between one error per $10^{14}$ bases and one error per $10^{17}$ bases (e.g., one error per $10^{14}$, per $10^{15}$, per $10^{16}$, or per $10^{17}$ bases) of processed, compressed genomic data. Of the bits storing genomic data, a solid state drive can have an average error rate between one error per $10^{12}$ bases and one error per $10^{15}$ bases (e.g., one error per $10^{12}$, per $10^{13}$, per $10^{14}$, or per $10^{15}$ bases) of processed, compressed genomic data.

Another aspect of the compression methods provided herein is the ratio of the error rate associated with bases stored as an uncompressed text file to the error rate of bases stored following compression of a genomic data set according to a method provided herein. When genomic data is compressed according to the methods provided herein, the ratio is 1:2, 1:3, 1:4, 1:5, 1:6, 1:18, 1:10, 1:15, or lower. In exemplary embodiments, the ratio is 1:4 or less.

The present invention has been described in terms of one or more preferred embodiments, and it should be appreciated that many equivalents, alternatives, variations, and modifications, aside from those expressly stated, are possible and within the scope of the invention.

EXAMPLES

Example 1

Obtaining a Biological Sample

An individual provides a biological sample (e.g., saliva, cheek cells, saliva or spit, semen, feces, hair, egg, biopsy, or blood) or is extracted during surgery (e.g., a tumor or healthy tissue). Alternatively, a sample is obtained from a surface or collection device. The sample is maintained in a state that preserves genomic or proteomic integrity, for example using specialized buffers or snap freezing the sample.

Example 2

Extracting Nucleic Acids

DNA and/or RNA is extracted using standard or specialized procedures. Standard procedures include but are not limited to the use of DNA or RNA extraction kits that lyse the cells with a buffer containing a protease (e.g., Proteinase K). The DNA or RNA containing solution is then passed through a purification column that binds the nucleic acid (e.g., glass beads). The contaminants are liberated by washing and the DNA is then eluted and stored frozen. Nucleic acids can also be extracted using chemicals that remove proteins and lipids such as phenol, then cleaned up with chloroform and ethanol precipitation.

Example 3

DNA Sequencing

Starting material for DNA sequencing library construction is usually double stranded DNA. Sources include genomic DNA, BACs, PCR amplicons, ChIP samples, any type of RNA turned into double stranded cDNA (mRNA, normalized total RNA, smRNAs). The dsDNA is then fragmented (e.g., with an average fragment length less than 600 bp in the case of HiSeq Illumina sequencing machines). The DNA ends are repaired and 'A' tailed, adapters are ligated on, size selection is carried out, then a polymerase chain reaction (PCR) is performed to generate the library for sequencing. The input DNA and RNA quantities specified below apply if the samples are quantified by a fluorometric method (e.g. Qubit, PicoGreen, RiboGreen). Numerous companies provide services and platforms that generate whole exome or target amplification. RNA-seq library preparation can include methods to increase target selection such as ribo-depletion, poly-A enrichment, strand-specific libraries, micro-RNA (miRNA) and small RNA libraries. Libraries can be generated without PCR to reduce bias and are useful for coverage of specific genomic areas such as GC-rich regions, promoters, and repeat regions, and sequence variants. Indexing or barcoding allows for the sequencing of multiple libraries in a single lane, i.e., multiplexing. Commercial kits are often used to generate the sequencing library. These are available from Illumina, IntegenX, NEB, Kapa Biosystems, Bioo Scientific, CloneTech, and NuGen. The library may be sequenced on any one of a number of DNA sequencing platforms using platform-specific reactions and detection methods as described above.

Example 4

Compression of Sequence Data

The sequence data is transferred to configured to a data compression system. The data compression system assigns a binary number to each of the primary characters in the sequence. The primary character 'A' is represented as 00; the primary character 'C' is represented as 01; the primary character 'G' is represented as 10; and the primary character 'T' is represented as 11.

Example 5

Compression With Secondary Characters

Secondary characters are removed as outlined in FIG. 3. After obtaining a string composed of nucleotides, each nucleotide is read. If the nucleotide is a secondary character (regarded as N), then the position of N is saved within the sequence and reading continues along the sequence. If the read is not an N, then the nucleotide is converted to its binary representation (as shown in FIG. 3, but other embodiments could have a different mapping) and stored in a register according to certain mathematical or computational operations (detailed below). If the register is full save it and read the next sequence element until the last element of the sequence is reached. In other embodiments, the first element could be 2 bytes long, but the rest could be 1 byte long if the difference between them is smaller than 256 by using delta-encoding. In other cases, the number of bytes could be variable for each element.

Example 6

Storing the Binary Representation of Nucleotides Using Registers

As shown in FIG. 3, the binary representation is stored in a register. The first element is saved in the first two bits of the register, the second in the third and fourth, the third in the fifth and sixth bits, and the fourth element is saved in the seventh and eighth bits. In other embodiments, the nucleotides can be stored in a different order.

Example 7

Transfer of Compressed Data

Compressed data is then transferred to a separate computing device such as a storage unit. In some cases, the separate computing device is a compute unit, where the more light-weight format can be used. As the compressed data is transferred, the receiving computing device can begin decompressing data to perform operations related to the data aforementioned.

Example 8

Decompression of Sequence Data

The compressed data format includes a field specifying the length of the sequence data and a set of registers. As each register from the compressed data is read, the number saved to the register is translated to its 4-letter code assigned in the tables below. These sequences are stored in memory or in a separate file. If the length of the sequence is not a multiple of four (4), the last register is translated using a lookup table corresponding to 3 letters, 2, letters, or 1 letter, depending on the remainder integer. When the sequence has been fully decoded, the file is closed.

We claim:

1. A method for preparing and analyzing DNA comprising:
   a. obtaining from a subject a sample, wherein the sample comprises DNA;
   b. preparing the sample for DNA sequencing to obtain a prepared sample;
   c. performing a sequencing reaction on the prepared sample using a sequencer to obtain raw sequence information comprising a plurality of primary characters each corresponding to one of a plurality of molecular units, wherein the raw sequence information includes at least 100 primary characters;
   d. transmitting the raw sequence information to a computing device;
   e. identifying a position in the raw sequence information corresponding to a secondary character representing a molecular unit that is not positively identified as corresponding to one of the plurality of primary characters;
   f. removing the secondary character from the raw sequence information;
   g. encoding the position of the secondary character as first position information;
   h. transforming the raw sequence information, excluding at least the secondary character, into a compressed data set using a fixed encoding scheme;
   i. transferring the compressed data set and the first position information to a computer memory, wherein the compressed data set and first position information utilizes less than 80% of the memory required for the raw sequence information before compression; and
   j. accessing the transferred compressed data set and the first position information from the computer memory using with a graphical user interface (GUI) the computer memory to retrieve and visualize genomic information.

2. The method of claim 1, wherein the compressed data set is associated with the fixed encoding scheme such that the compressed data set is identifiable by the fixed encoding scheme.

3. The method of claim 1, further comprising identifying in the raw sequence information at least one nucleotide sequence.

4. The method of claim 3, wherein each of the plurality of molecular units is a nucleotide base of a plurality of nucleotide bases.

5. The method of claim 4, wherein the plurality of nucleotide bases comprises adenine (A), thymine (T), guanine (G), and cytosine (C).

6. The method in claim 3, further comprising the step of assigning a binary number to each of the plurality of primary characters when applying the fixed encoding scheme to the at least one nucleotide sequence.

7. The method in claim 6, further comprising the step of receiving quality data associated with the raw sequence data, wherein the at least one nucleotide sequence being encoded is free of quality data.

8. The method in claim 7, further comprising the step of applying a separate, fixed encoding scheme to the quality data.

9. The method of claim 1, wherein the raw sequence information is a FASTQ file.

10. The method of claim 1, wherein the DNA is chromosomal, viral, or mitochondrial DNA.

11. A method comprising:
   receiving at least one genomic data set, the genomic data set comprising a plurality of primary characters each corresponding to one of a plurality of molecular units, and a secondary character representing a molecular unit that is not positively identified as corresponding to one of the plurality of primary characters, wherein the genomic data set includes at least 100 primary characters;

identifying a position in the genomic data set corresponding to the secondary character;

removing the secondary character from the position in the genomic data set;

encoding the position of the secondary character as first position information;

generating, using a fixed encoding scheme, a compressed data set that excludes at least the secondary character, wherein the fixed encoding scheme compresses genomic sequence information of the at least one genomic data set at a density of four base pairs per byte;

transferring the compressed data set and the first position information to a computer memory, wherein the compressed data set and the first position information utilizes less than 80% of the memory required for the received genomic data set before compression; and accessing the transferred compressed data set and the first position information from the computer memory using a graphical user interface (GUI) the computer memory to retrieve and visualize genomic information.

12. The method of claim 11, wherein metadata associated with the at least one genomic data set is not encoded at a density of four base pairs per byte and is stored separately from the transferred compressed data set.

13. The method in claim 12, further comprising the step of applying a separate, fixed encoding scheme to the metadata associated with the at least one genomic data set.

14. The method in claim 11, wherein encoding comprises assigning at least one of adenine (A), thymine (T), guanine (G), and cytosine (C) to a two-bit binary number.

15. The method in claim 11, wherein the compression is lossless.

16. The method in claim 15, wherein the compression of the genomic data with secondary characters removed is up to 75 percent compared to the received genetic data set prior to encoding.

17. The method of claim 11, wherein the interface is configured to display genomic data.

18. A method comprising:

receiving genomic data via a processor, the genomic data comprising a plurality of primary characters each corresponding to one of a plurality of molecular units, and a secondary character representing a molecular unit that is not positively identified as corresponding to one of the plurality of primary characters, wherein the genomic data includes at least 100 primary characters; and identifying a position in the genomic data corresponding to the secondary character;

removing the secondary character from the position in the genomic data;

encoding the position of the secondary character as first position information;

encoding nucleic acid sequence information of the genomic data, subsequent to removal of the secondary character from the genomic data, at a density of four base pairs per byte, wherein the encoding achieves compression such that the compressed, encoded nucleic acid sequence information and first position information uses less than 80% of the computer memory required to store the genomic data prior to encoding.

19. The method of claim 18, wherein non-nucleic acid sequence information of the genomic data is not compressed and is stored separately from the encoded nucleic acid sequence information.

20. The method of claim 19, further comprising reconstructing an uncompressed genomic data set from the compressed nucleic acid sequence information, wherein reconstructing comprises applying a fixed decoding scheme to the encoded nucleic acid sequence information to obtain uncompressed nucleic acid sequence information;

retrieving non-nucleic acid sequence information from the separate storage; and adding the non-nucleic acid sequence information to the uncompressed nucleic acid information to obtain a reconstructed genomic data set.

21. The method of claim 1, further comprising:

identifying a plurality of positions, including the position, in the raw sequence information each corresponding to the secondary character representing a molecular unit that is not positively identified as corresponding to one of the plurality of primary characters;

removing each of the secondary characters from the raw sequence information;

encoding each position of the plurality of positions using at least one byte; and storing position information corresponding to each position separately from the compressed data set.

22. The method of claim 1, wherein the raw sequence information includes at least 250 primary characters.

23. The method of claim 1, wherein the raw sequence information includes at least 1000 primary characters.

24. The method of claim 11, wherein the genomic data set includes at least 250 primary characters.

25. The method of claim 18, wherein the genomic data set includes at least 250 primary characters.

* * * * *